United States Patent [19]

Yoda et al.

[11] Patent Number: 5,061,777
[45] Date of Patent: Oct. 29, 1991

[54] THROMBORESISTANT POLYETHERURETHANE COMPOUNDS AND PROCESS FOR ITS PRODUCTION

[75] Inventors: Ryuichiro Yoda; Akira Fukutome; Suguru Ohkawa; Kazutoshi Iida, all of Yokohama, Japan

[73] Assignee: Nippon Zeon Co., Ltd., Tokyo, Japan

[21] Appl. No.: 554,164

[22] Filed: Jul. 19, 1990

Related U.S. Application Data

[63] Continuation of Ser. No. 168,570, Mar. 7, 1988, abandoned, which is a continuation of Ser. No. 832,405, Feb. 24, 1986, abandoned.

[30] Foreign Application Priority Data

Feb. 28, 1985 [JP]  Japan .................................. 60-39981

[51] Int. Cl.$^5$ .............................................. C08G 18/48
[52] U.S. Cl. ......................................... 528/61; 528/62; 528/64; 528/76; 604/262; 604/266; 604/269
[58] Field of Search ....................... 604/262, 266, 269; 528/61, 62, 64, 76

[56] References Cited

U.S. PATENT DOCUMENTS 4,371,686  2/1983  Yamamoto et al. ................... 528/61
4,523,005  6/1985  Szycher ................................ 528/76
4,942,214  7/1990  Sakhpara ............................. 528/66

OTHER PUBLICATIONS

Heiss, H. L. et al., Industrial & Engineering Chemistry 46, 1498 (1954).
Saunders, J. H. et al., Polyurethanes, Chemistry & Technology Part I Chemistry, 293-314 (1963).
Hepburn, C.: Polyurethane Elastomers, 50-54 (1982).

Primary Examiner—Veronica P. Hoke
Attorney, Agent, or Firm—Sherman & Shalloway

[57] ABSTRACT

A thromboresistant segmented polyetherurethane compound wherein the polyether segment consists of 99 to 1% by weight of (a) a polytetramethylene ether segment having a number average molecular weight of 200 to 5,000 and 1 to 99% by weight of (b) a polyalkylene ether segment having a number average molecular weight of 200 to 5,000 in which the alkylene group has 2 or 3 carbon atoms, said segments (a) and (b) being contained in the same main chain. The segmented polyetherurethane compound is produced by a process comprising reacting 99 to 1% by weight of a polytetramethylene ether diol having a number average molecular weight of 200 to 5,000 and 1 to 99% by weight of a polyalkylene ether diol having a number average molecular weight of 200 to 5,000 in which the alkylene group has 2 or 3 carbon atoms, with a polyisocyanate compound, and reacting the resulting prepolymer with a chain extender.

11 Claims, No Drawings

THROMBORESISTANT POLYETHERURETHANE COMPOUNDS AND PROCESS FOR ITS PRODUCTION

This application is a continuation of application Ser. No. 07/168,570 filed Mar. 7, 1988 which is a continuation of Ser. No. 06/832,405 filed Feb. 24, 1986 now abandoned.

This invention relates to a novel segmented polyurethane compound having excellent thromboresistance and favorable dynamic properties, and a process for its production. More specifically, this invention relates to a thromboresistant segmented polyetherurethane compound comprising in the same main chain a hydrophobic polytetramethylene ether segment and a hydrophilic polyalkylene ether segment as polyether segments, and a process for producing a thromboresistant segmented polyurethane compound comprising reacting isocyanate-terminated prepolymers for formation of the individual polyether segments with a chain extender.

Known thromboresistant elastomers include, for example, a segmented linear polyurethane or polyurethaneurea comprising polytetramethylene ether as a soft segment and methylene-bis(4-phenyl) radical as a hard segment [e. g., Biomer of Ethicon Co., or Techoflex of Thermo Electron Co. described in Elastomerics, Mar., 11-15 (1983)] produced by the method disclosed in U.S. Pat. No. 3,804,812; heparinized polyurethane (U.S. Pat. No. 3,766,104); and a block copolymer in which polysiloxane and polyurethane are directly bonded through silicon-nitrogen (U.S. Pat. No. 3,562,352).

These conventional polymeric materials, however, are not enough to meet a broad rang of requirements. For example, the known segmented polyurethane has high mechanical strength but does not have sufficient thromboresistance. With the heparinized polyurethane, heparin is released within a short period of time, and after the releasing of heparin, its thromboresistance is extremely reduced. Among the existing materials, the block copolymer of polysiloxane and polyurethane directly bonded through silicon-nitrogen has the best thromboresistance as demonstrated by many clinical tests. However, since the level of thromboresistance varies depending upon molding conditions for the copolymer, a strict process control is required in order to form a blood contacting surface which gives a constant level of excellent thromboresistance.

During the course of our research and development work for a new material having excellent dynamic properties and high thromboresistance and permitting easy process control, we found that the use of a hydrophilic segmented polyurethane containing polyethylene ether, polypropylene ether, ethylene oxide/propylene oxide random copolymer, polyethylene oxide/polypropylene oxide block copolymer, etc. as a soft segment develops higher thromboresistance than a known hydrophobic segmented polyurethane containing polytetramethylene ether as a soft segment. This polyurethane containing a hydrophilic polyether as a soft segment, however, has been found to have very high tackiness and low mechanical strength and be useless in practical applications.

We therefore made extensive investigations in order to develop a practical segmented polyurethane by taking advantage of the characteristic of polyurethane containing a hydrophilic polyether having excellent thromboresistance as a soft segment, and these investigations have now led to the present invention.

It is an object of this invention to provide a segmented polyetherurethane compound having excellent dynamical properties and thromboresistance, and a process for its production.

Thus, according to this invention, there is provided a thromboresistant segmented polyetherurethane compound wherein the polyether segment consists of 99 to 1% by weight of (a) a polytetramethylene ether segment having a number average molecular weight of 200 to 5,000 and 1 to 99% by weight of (b) a polyalkylene ether segment having a number average molecular weight of 200 to 5,000 in which the alkylene group has 2 or 3 carbon atoms, said segments (a) and (b) being contained in the same main chain.

According to this invention, there is also provided a process for producing a thromboresistant segmented polyetherurethane compound, which comprises reacting 99 to 1% by weight of a polytetramethylene ether diol having a number average molecular weight of 200 to 5,000 and 1 to 99% by weight of a polyalkylene ether diol having a number average molecular weight of 200 to 5,000 in which the alkylene group has 2 or 3 carbon atoms, with a polyisocyanate compound, and reacting the resulting prepolymer with a chain extender.

The polyurethane compound, as used in this invention, denotes both polyurethane and polyurethaneurea.

The polyurethane compound produced by the process of this invention is a segmented polyurethane or polyurethaneurea containing a hydrophobic polytetramethylene ether segment and a hydrophilic polyalkylene ether segment with the alkylene group having 2 or 3 carbon atoms in the same main chain, and can be favorably used in the construction of various blood-contacting medical instruments, an intra-aortic balloon pump, and artificial organs such as artificial hearts by making use of its thromboresistance, mechanical strength and the ease of process control.

Examples of the polyalkylene ether diol with the alkylene group having 2 or 3 carbon atoms used in producing the hydrophilic polyether segment in this invention include polyethylene ether glycol, polypropylene ether glycol, a hydroxy-terminated random copolymer derived from ethylene oxide and propylene oxide, and a hydroxy-terminated block copolymer composed of (A) polyethylene oxide blocks and (B) polypropylene oxide blocks. The block copolymers may be of any of the AB, ABA and BAB types.

The content of ethylene oxide in the random copolymer and block copolymers is usually in the range of 10 to 90% by weight, preferably 30 to 70% by weight. If it is less than 10% by weight, sufficient thromboresistance cannot be obtained. If it exceeds 90% by weight, the mechanical strength of the resulting polyurethane compound is low.

These polymers have a number average molecular weight of 200 to 5,000. If it is less than 200, sufficient thromboresistance cannot be obtained. If it exceeds 5,000, the mechanical strength of the resulting polyurethane compound is low. The preferred number average molecular weight of these polymers is 500 to 3,000.

The segmented polyurethane compound of this invention having a hydrophobic polyether segment and a hydrophilic polyether segment in the same main chain, i.e. polyurethane or polyurethaneurea, can be produced by reacting the hydrophilic polytetramethylene ether diol and the hydrophilic polyalkylene ether diol with a polyisocyanate compound, and reacting the resulting isocyanate-terminated prepolymer with a chain extender. The prepolymer may be produced, for example, by reacting a mixture of the polyether diols with the polyisocyanate compound to form a prepolymer mixture; or reacting the two polyether diols individually with the polyisocyanate compounds to produce two isocyanate-terminated prepolymers. The latter procedure is preferred from the standpoint of thromboresistance.

The prepolymer-forming reaction can be carried out in the absence of a solvent. Preferably, however, it is carried out in the presence of solvents used in the production of ordinary polyurethane compounds. Preferred solvents include, for example, N,N-dimethylformamide, N,N-dimethylacetamide, dimethyl sulfoxide, tetrahydrofuran, 1,4-dioxane, N-methylpyrrolidone, and mixtures containing these solvents in a major proportion. There is no particular restriction on the reaction temperature, but temperatures of 40° to 130° C. are preferred.

Catalysts used in the production of ordinary polyurethane compounds may also be used in the process of this invention. For medical applications, easily removable catalysts such as triethylenediamine and diazabicycloundecene are especially preferred.

All polyisocyanate compounds heretofore used in the formation of polyurethane can be used in this invention, but diisocyanate compounds are especially preferred. Examples include tetramethylene diisocyanate, hexamethylene diisocyanate, trimethylhexamethylene diisocyanate, cyclohexane 1,4-diisocyanate, isophorone diisocyanate, 2,4-tolylene diisocyanate, 2,6-tolylene diisocyanate, a mixture of 2,4-tolylene diisocyanate and 2,6-tolylene diisocyanate, xylylene diisocyanate, 4,4'-diphenylmethane diisocyanate, 1,4-phenylene diisocyanate, 4,4'-dicyclohexylmethane diisocyanate, 1,3-phenylene diisocyanate, and naphthalene 1,5-diisocyanate. They may be used either singly or as a mixture.

A chain extender is added to, and reacted with, the resulting prepolymer mixture solution or a solution of the resulting two prepolymer solutions to form the polyurethane compound of this invention.

In order for the polyurethane compound of this invention to exhibit excellent thromboresistance and mechanical strength, the proportions of the hydrophobic polyether and the hydrophilic polyether in the same main chain are especially important. In the entire polyether segments, the content of the hydrophilic polyether should be 1 to 99% by weight, preferably 5 to 80% by weight, more preferably 10 to 60% by weight. If it is less than 1% by weight, thromboresistance is insufficient, and if it exceeds 99% by weight, the mechanical strength of the polyurethane compound is reduced so much that it is not suitable for practical applications. Desirably, therefore, the two prepolymers are mixed so that the proportions of the two polyethers in the final polyurethane compound are within the above-specified ranges, and the mixture is then reacted with the chain extender.

Difunctional chain extenders having active hydrogens are suitable as the chain extender used in this invention. Examples include aliphatic diamines such as ethylenediamine, propylenediamine, butylenediamine and hexamethylenediamine; alicyclic diamines such as cyclohexanediamine; aromatic diamines such as phenylenediamine, diphenylmethanediamine and xylylenediamine; heterocyclic diamines such as piperazine; hydrazine; diols such as ethylene glycol, propylene glycol, diethylene glycol, dipropylene glycol, 1,4-butanediol, neopentyl glycol and cyclohexane dimethanol; water; and ethanolamine.

In order to obtain thromboresistance, it is undesirable for the segmented polyurethane compound to be highly crosslinked. Desirably, it is essentially thermoplastic elastomer. Accordingly, when a trifunctional or higher compound such as trimethylolpropane, glycerol or N,N,N',N'-tetrakis(2-hydroxypropyl)ethylenediamine is used as a chain extender, its amount should be such as not to reduce the thermoplasticity of the resulting polyurethane compound.

The chain-extending reaction is carried out usually under ice cooling or under heat. In the production of the polyurethane compound of this invention, the amounts of the polyether diol, the diisocyanate compound and the chain extender used may be those conventionally used. Usually, about 2 moles of the diisocyanate and about 1 mole of the chain extender are used per mole of the polyether diol.

The segmented polyurethane compound so synthesized is used as a solution or in a dried state after precipitating it from the solution, washing it fully with water or ethanol and repeating precipitation to remove impurities.

Blood-contacting medical devices may be produced by using the polyurethane compound of this invention as a solution in accordance with a coating method, dipping method or casting method. Or they may be produced by pelletizing the polyurethane compound and molding the pellets by ordinary molding methods for thermoplastic synthetic resins, such as extrusion, injection molding or compression molding. The polyurethane compound of this invention is very stable during storage either a pellets or a solution, and no molecular disintegration occurs under the effect of moisture. Accordingly, it is easy to handle, and has good reproducibility and excellent properties as a thromboresistant elastomer.

It is said that the desirable-dynamic properties of the thromboresistant elastomer are generally shown by a tensile strength of at least 100 kg/cm$^2$ and an elongation of 300 to 500% or higher. The polyurethane elastomer in accordance with this invention has a tensile strength of 100 to 500 kg/cm$^2$ and an elongation of at least 500%, and thus shows excellent dynamical properties.

Accordingly, the thromboresistant polyurethane compound of this invention can be suitably used in a blood-contacting surface of medical devices used in direct contact with blood. Specific examples of such devices are devices for handling or storing blood having a blood-contacting surface such as blood bags, intra-blood vessel indwelling catheters and cannulae, and devices for extra-corporeal circulation of blood such as artificial kidneys, artificial hearts and balloon pumps.

The following examples further illustrate the present invention. All parts and percentages in these examples are by weight unless otherwise specified.

EXAMPLE 1

A reaction vessel fully dried by heating in a nitrogen stream was charged with 30 g (0.03 mole) of a hydroxy-terminated ethylene oxide-propylene oxide random copolymer (ADEKA POLYETHER PR-1003, a trade name for a product of Asahi Denka Kogyo K. K., having a molecular weight of 1,000 and an ethylene oxide content of 30%). The copolymer was dehydrated at 80° C. under a reduced pressure of less than 0.1 mmHg for 2 hours. The temperature was lowered to 50° C., and dehydrated and purified dimethylacetamide was added in a weight 50 times the weight of the copolymer. Thereafter, in a customary manner, 15 g (0.06 mole) of 4,4'-diphenylmethane diisocyanate was added, and the mixture was stirred for 2 hours to form a prepolymer (1).

In the same way as above, 30 g (0.046 mole) of hydroxy-terminated polytetramethylene ether (molecular weight 650) and 23 g (0.092 mole) of 4,4'-diphenylmethane diisocyanate were reacted in dehydrated and purified dimethylacetamide in a separate reaction vessel to form a prepolymer (2).

The prepolymer (1) solution and the prepolymer (2) solution were mixed so that the weight ratio of the two polyether diols became 1:1. Then, 6.8 g (0.076 mole) of 1,4-butanediol was added to the mixure, and reacted with stirring at 80° C. for 6 hours to synthesize polyurethane.

Polyurethane urea was synthesized under the same conditions as above except that 4.6 g (0.076 mole) of ethylenediamine was used instead of 1,4-butanediol.

After each of the above reactions, the reaction solution was added dropwise to methanol to precipitate polyurethane or polyurethaneurea. Each precipitate was washed with methanol three times to purify the polyurethane compound, and then it was dried under reduced pressure.

The resulting polyurethane compounds had a molecular weight, measured by GPC using tetrahydrofuran as a solvent, of 29,000 and 30,000, respectively.

EXAMPLE 2

In the same way as in Example 1, (a) a hydroxy-terminated ethylene oxide/propylene oxide random copolymer (ADEKA POLYETHER PR-1007, a trade name for a product of Asahi Denka Kogyo K. K., having a molecular weight of 1,000 and an ethylene oxide content of 70%) and (b) a hydroxy-terminated polytetramethylene ether (molecular weight 650) were individually reacted with 4,4'-diphenylmethane diisocyanate to form prepolymers in solution.

These prepolymer solutions were mixed so that the weight ratio of the polymer (a) to the polymer (b) became 3:2. The mixture was reacted with 1,4-butanediol as a chain extender to synthesize polyurethane. The product was purified as in Example 1 to give purified polyurethane having a molecular weight of 32,000.

Polyurethaneurea was also synthesized in the same way as in Example 1.

EXAMPLE 3

In the same way as in Example 1, (c) a hydroxy-terminated ethylene oxide/propylene oxide block copolymer (ADEKA POLYETHER CM-164, a trade name for a product of Asahi Denka Kogyo K. K., having a molecular weight of 1,600 and an ethylene oxide content of 40%) and (d) a hydroxy-terminated polytetramethylene ether (molecular weight 650) were individually reacted with 4,4'-diphenylmethane diisocyanate to form prepolymers in solution.

These prepolymer solutions were mixed so that the weight ratio of the polymer (c) to the polymer (d) became 4:1. The mixture was reacted with 1,4-butanediol as a chain extender to synthesize polyurethane. The product was purified as in Example 1 to give purified polyurethane having a molecular weight of 31,000.

EXAMPLE 4

In the same way as in Example 1, (e) a hydroxy-terminated polyethylene ether (molecular weight 1,000) and (f) a hydroxy-terminated polytetramethylene ether (molecular weight 1500) were individually reacted with 4,4'-diphenylmethane diisocyanate to form prepolymers in solution.

These prepolymer solutions were mixed so that the weight ratio of the polymer (e) to the polymer (f) became 1:4. The mixture was reacted with 1,4-butanediol as a chain extender to synthesize polyurethane. The product was purified as in Example 1 to give purified polyurethane having a molecular weight of 40,000.

EXAMPLE 5

Polyurethane was synthesized in the same way as in Example 1 except that the prepolymer solutions were mixed so that the weight ratio of the hydrophilic polyether to the hydrophobic polyether became 1:4.

COMPARATIVE EXAMPLE 1

Polyurethane was synthesized in the same way as in Example 1 by reacting a hydroxy-terminated ethylene oxide/propylene oxide random copolymer (molecular weight 1,000, ethylene oxide content 70%) with 4,4'-diphenylmethane diisocyanate and then with 1,4-buanediol as a chain extender.

COMPARATIVE EXAMPLE 2

Polyurethane was synthesized in the same way as in Example 1 by reacting a hydroxy-terminated polytetramethylene ether (molecular weight 650) with 4,4'-diphenylmethane diisocyanate and then with 1,4-buanediol as a chain extender.

EXAMPLE 6

Each of the nine polyurethane compounds prepared in Examples 1 to 5 and Comparative Examples 1 and 2 above was dissolved in a 2:1 by weight mixture of tetrahydrofuran and dioxane or N,N-dimethylacetamide in a concentration or 10% by weight. The solution was cast onto a glass plate to form a film. The film was colorless and transparent, and was found to have a very smooth surface by observation under a scanning electron microscope.

A water droplet was dropped onto the film, and the contact angle formed between the film surface and the water droplet was measured by a goniometer-type contact angle meter.

In the measurement of thromboresistance, the above polymer solution was coated twice on the inner wall of a test tube, and the solvent was fully evaporated. By using the resulting inside-coated test tube inside diameter 10 mm, length 100 mm), the blood coagulation time was measured by the Lee White method.

The above polymer solution was coated on polyester yarns (No. 2-)), and dried by fully evaporating the solvent. The yarns were each inserted to an extent of about 10 cm into the vessel of the jugular vein and the vessel of the femoral vein of a dog weighing 5 to 15 kg through an injection syringe. One end of each yarn was fixed, and the yarn was left to stand (peripheral vein insertion method). One day later, heparin was injected intravenously into the dog, and the dog was bled to death. The vessels were cut open, and the state of thrombus adhering to the inserted yarns were observed.

The above film was removed from the glass plate and cut into a rectangular shape. The strengths properties of the rectangular sample were measured at a stretching speed of 200 mm/min.

The results are shown in Table 1.

TABLE 1

| | Polyurethane compound | | | Blood coagulating time (minutes) | State of thrombus adhesion by the peripheral vein insertion method | Contact angle *2 | Tensile strength (kg/cm$^2$) | Elongation (%) |
|---|---|---|---|---|---|---|---|---|
| | Proportions of the polyether segments (%) | | Kind *1 | | | | | |
| | Hydrophilic segment | Hydrophobic segment | | | | | | |
| Example 1 | 50 | 50 | U | 105 | No adhesion | 5.27 ± 2.1 | 530 | 500 |
| | | | UU | 100 | " | | 600 | 450 |
| Example 2 | 60 | 40 | U | 110 | " | 40.5 ± 1.3 | 500 | 550 |
| | | | UU | 110 | " | | 540 | 500 |
| Example 3 | 80 | 20 | U | 110 | " | 47.5 ± 1.3 | 400 | 600 |
| Example 4 | 20 | 80 | U | 105 | " | 60.3 ± 3.0 | 560 | 500 |
| Example 5 | 20 | 80 | U | 110 | " | 58.4 ± 2.3 | 500 | 500 |
| Comparative Example 1 | 100 | — | U | 70 | Adhesion in a small amount | 30.0 ± 4.2 | 80 | 300 |
| Comparative Example 2 | — | 100 | U | 56 | Adhesion in a large amount | 64.7 ± 3.1 | 530 | 500 |
| Control | Glass test tube *3 | | | 9–13 | — | — | — | — |

Note
*1 U stands for polyurethane; UU, polyurethaneurea
*2 An average value of four measurements of each sample
*3 Not coated with the polyurethane compound

EXAMPLE 7

The inside surface of a snack-type blood pump of polyvinyl chloride was coated with the polyurethane or polyurethaneurea prepared in Examples 1, 2 or 3. The coating was carried out by dissolving the polyurethane compound in a 2:1 mixture of tetrahydrofuran and dioxane, filling the solution in the blood pump, immediately then removing it by inclining the pump, and then drying the pump in air.

This blood pump was used as a left ventricular assist of a goat. The stroke volume of the blood pump was 40 ml. The assisting was carried out for 7 days while maintaining the rate of discharge at 80 cycles/min. and the amount of discharge at 2 liters/min., and then the blood pump was exchanged with a new one.

The state of adhesion of thrombus to the used blood pump was examined. It was found that no adhesion of thrombus was observed on the inner surfaces of the blood pumps coated with the polyurethane compounds prepared in Examples 1, 2 and 3.

The surface of the blood pump was very smooth when observed under a scanning electron microscope, and no cracking owing to the fatigue of polyurethane was noted. Peeling of the polyurethane coating on the inside surface of the blood pump was neither observed.

What we claim is:

1. A thromboresistant segmented polyurethane compound wherein the polyether segment consists of 90 to 40% by weight of (a) a polytetramethylene ether segment having a number average molecular weight of 200 to 5,000 and 10 to 60% by weight of (b) a polyalkylene ether segment having a number average molecular weight of 200 to 5,000 in which the alkylene group has 2 or 3 carbon atoms or mixtures thereof, said segments (a) and (b) being contained in the same main chain.

2. The segmented polyetherurethane compound of claim 1 wherein the polyalkylene ether segment (b) is at least one polymer selected from the group consisting of polyethylene ether, polypropylene ether, ethylene oxide/propyleneoxide random copolymer and polyethyene oxide/polypropylene oxide block copolymer.

3. The segmented polyetherurethane compound of claim 1 or 2 which is segmented polyurethane.

4. The segmented polyetherurethane compound of claim 1 or 2 which is segmented polyurethaneurea.

5. A medical device having a blood-contact surface which is formed from the polyetherurethane compound of claim 1.

6. A process for producing a thromboresistant segmented polyurethane compound which comprises reacting 90 to 40% by weight of a polyalkylene ether diol having a number average molecular weight of 200 to 5,000 and 10 to 60% by weight of a polyalkylene ether diol having a number average molecular weight of 200 to 5,000 in which the alkylene group has 2 or 3 carbon atoms or mixtures thereof, with a polyisocyanate compound, and reacting the resulting prepolymer with a chain extender.

7. The process of claim 6 wherein the polyalkylene ether diol is at least one diol selected from the group consisting of polyethylene ether glycol, polypropylene ether glycol, ethylene oxide/propylene oxide copolymer diol, and polyethylene oxide-polypropylene oxide block copolymer diol.

8. The process of claim 5 wherein a mixture of prepolymer derived from the polytetramethylene ether diol and polyisocyanate compound and a prepolymer derived from polyalkylene ether diol and polyisocyanate compound is reacted with the chain extender.

9. The process of claim 6 wherein a prepolymer derived from the polyisocyanate compound and a mixture of the polytetramethylene ether diol and the polyalkylene ether diol is reacted with the chain extender.

10. The process of any of claims 6, 7, 8, or 9 wherein the polyisocyanate compound is a diisocyanate compound.

11. The process of any one of claims 6, 7, 8 or 9 wherein the chain extender is a low-molecular weight diol or a diamine.

* * * * *